(12) United States Patent
Yasuda

(10) Patent No.: US 9,915,604 B2
(45) Date of Patent: Mar. 13, 2018

(54) GAS CONCENTRATION MEASUREMENT DEVICE

(71) Applicant: Murata Manufacturing Co., Ltd., Nagaokakyo-shi, Kyoto-fu (JP)

(72) Inventor: Masaaki Yasuda, Nagaokakyo (JP)

(73) Assignee: Murata Manufacturing Co., Ltd., Kyoto (JP)

( * ) Notice: Subject to any disclaimer, the term of this patent is extended or adjusted under 35 U.S.C. 154(b) by 0 days.

(21) Appl. No.: 15/382,772

(22) Filed: Dec. 19, 2016

(65) Prior Publication Data

US 2017/0102324 A1 Apr. 13, 2017

Related U.S. Application Data

(63) Continuation of application No. PCT/JP2015/066874, filed on Jun. 11, 2015.

(30) Foreign Application Priority Data

Jul. 3, 2014 (JP) .................................. 2014-137788

(51) Int. Cl.
*G01N 21/00* (2006.01)
*G01N 21/3504* (2014.01)
(Continued)

(52) U.S. Cl.
CPC ......... *G01N 21/3504* (2013.01); *G01N 21/61* (2013.01); *G01N 33/004* (2013.01); *G01N 2201/0686* (2013.01)

(58) Field of Classification Search
CPC .. G01N 21/3504; G01N 21/61; G01N 33/004; G01N 2201/0686
See application file for complete search history.

(56) References Cited

U.S. PATENT DOCUMENTS 3,735,127 A * 5/1973 Astheimer .......... F02D 41/1451
250/339.13
3,832,548 A * 8/1974 Wallack ............. G01N 21/3504
250/343
(Continued)

FOREIGN PATENT DOCUMENTS

JP 05-203573 A 8/1993
JP 2007-501404 A 1/2007
JP 2013-515963 A 5/2013

OTHER PUBLICATIONS

Official Communication issued in corresponding International Application PCT/JP2015/066874, dated Sep. 8, 2015.

*Primary Examiner* — Kara E Geisel
*Assistant Examiner* — Maurice Smith
(74) *Attorney, Agent, or Firm* — Keating & Bennett, LLP

(57) ABSTRACT

A gas concentration measurement device includes a waveguide including an entrance and an exit, a rotating member, first and second band pass filters on the rotating member and on a pair of planes that intersect each other, and a rotational driver. The rotating member is rotated by the rotational driver so that the first and second band pass filters are selectively located at a transmitting position. When a portion of the rotating member, the first band pass filter, or the second band pass filter, the portion having a maximum radius of gyration around a rotating shaft, is defined as a maximum radius portion, and when a rotation locus obtained by imaginarily rotating the maximum radius portion around the rotating shaft in a view along the rotating shaft is defined as a reference circle, the exit is located in the reference circle.

20 Claims, 11 Drawing Sheets

(51) Int. Cl.
*G01N 21/61* (2006.01)
*G01N 33/00* (2006.01)

(56) References Cited

U.S. PATENT DOCUMENTS

| | | | | |
|---|---|---|---|---|
| 5,542,285 | A * | 8/1996 | Merilainen | G01N 21/3504 250/343 |
| 5,739,535 | A * | 4/1998 | Koch | G01N 21/3504 250/338.3 |
| 6,811,751 | B1 * | 11/2004 | Olsson | G01N 21/3504 422/83 |
| 2010/0027004 | A1 * | 2/2010 | Bonyuet | G01J 3/02 356/326 |
| 2013/0119254 | A1 | 5/2013 | Russell | |

* cited by examiner

GAS CONCENTRATION MEASUREMENT DEVICE

CROSS REFERENCE TO RELATED APPLICATIONS

This application claims the benefit of priority to Japanese Patent Application No. 2014-137788 filed on Jul. 3, 2014 and is a Continuation Application of PCT Application No. PCT/JP2015/066874 filed on Jun. 11, 2015. The entire contents of each application are hereby incorporated herein by reference.

BACKGROUND OF THE INVENTION

1. Field of the Invention

The present invention relates to an infrared-light-absorption gas concentration measurement device.

2. Description of the Related Art

A gas concentration measurement device that uses the non-dispersive infrared (NDIR) absorption method is an example of a known concentration measurement device for measuring the concentration of a specific component contained in sample gas or the like. This type of gas concentration measurement device causes sample gas to absorb infrared light emitted from a light source, and then detects the amount of infrared light that has passed through an optical filter (band pass filter) with a detector. The concentration of the sample gas is determined on the basis of the amount of light with a specific wavelength that has been absorbed.

Japanese Unexamined Patent Application Publication No. 5-203573, for example, discloses such a gas concentration measurement device. The gas concentration measurement device disclosed in Japanese Unexamined Patent Application Publication No. 5-203573 is capable of measuring a plurality of types of sample gas by rotating a disc on which a plurality of band pass filters are arranged with intervals therebetween in a circumferential direction.

However, in the gas concentration measurement device disclosed in Japanese Unexamined Patent Application Publication No. 5-203573, the band pass filter to be used is switched by rotating the disc around a rotation axis that is parallel or substantially parallel to the direction in which the band pass filter and the detector are arranged during the measurement. The disc is relatively large because the band pass filters are arranged in the circumferential direction on the disc. Accordingly, the gas concentration measurement device is required to have a rotation region in which the disc rotates, and is therefore also large. It is difficult to install such a large gas concentration measurement device in a relatively small space.

SUMMARY OF THE INVENTION

Preferred embodiments of the present invention provide a gas concentration measurement device that is reduced in size.

A gas concentration measurement device according to a preferred embodiment of the present invention, which measures a gas concentration based on an absorbance of sample gas in a region between a light source that emits infrared light and a detector including a light-receiving portion that receives the infrared light, includes a waveguide including a wave-guiding portion including a tubular inner peripheral surface, an entrance at one side of the wave-guiding portion and through which the infrared light from the light source is introduced, and an exit at the other side of the wave-guiding portion and guiding the infrared light that has passed through the wave-guiding portion toward the detector; a rotating member that is rotatable around a rotating shaft that intersects an axial direction of the waveguide; a first band pass filter and a second band pass filter that are provided on the rotating member and located on a pair of planes that intersect each other; and a rotational driver that rotates the rotating member around the rotating shaft. The rotating member is rotated by the rotational driver so that the first band pass filter and the second band pass filter are selectively located at a transmitting position at which the infrared light guided out of the exit is transmitted toward the detector. When a portion of the rotating member, the first band pass filter, or the second band pass filter, the portion having a maximum radius of gyration around the rotating shaft, is defined as a maximum radius portion, and when a rotation locus obtained by imaginarily rotating the maximum radius portion around the rotating shaft in a view along the rotating shaft is defined as a reference circle, the exit is located in the reference circle.

Thus, the exit of the waveguide is disposed near the transmitting position at which the first band pass filter or the second band pass filter is located. Switching between the state in which the first band pass filter is located at the transmitting position and the state in which the second band pass filter is located at the transmitting position is performed by rotating the rotating member around the rotating shaft that intersects the axial direction of the waveguide. Accordingly, the size of the gas concentration measurement device is able to be smaller than that in the case where a rotating member on which a plurality of band pass filters are arranged along a single plane is rotated around a rotation axis that is parallel or substantially parallel to the axial direction of a waveguide.

In a gas concentration measurement device according to a preferred embodiment of the present invention, preferably, when an end portion of the rotating member that is farthest from the detector in a state in which the first band pass filter is located at the transmitting position is defined as a distal end portion, the exit is closer to the detector than the distal end portion.

Accordingly, the infrared light is incident on the first band pass filter or the second band pass filter that is located at the transmitting position at a small incident angle. Therefore, the detection accuracy of the gas concentration measurement device is increased.

In a gas concentration measurement device according to a preferred embodiment of the present invention, preferably, a portion or entirety of an inner peripheral surface of the wave-guiding portion includes a tapered region including a cross section that decreases along a direction from the entrance to the exit. In this case, preferably, the waveguide reflects the infrared light that has entered the wave-guiding portion through the entrance in the tapered region, so that energy of the infrared light that is obliquely incident on the first band pass filter or the second band pass filter that is located at the transmitting position is reduced.

Accordingly, the infrared light that has entered the wave-guiding portion through the entrance is reflected in the tapered region, and the energy of the infrared light that is obliquely incident on the first band pass filter or the second band pass filter that is located at the transmitting position is able to be reduced. Therefore, the measurement sensitivity of the gas concentration measurement device is increased.

Preferably, a gas concentration measurement device according to a preferred embodiment of the present invention further includes a surrounding frame that surrounds a periphery of the rotating member. In this case, preferably, the surrounding frame includes a peripheral wall that defines a rotation space, which enables the rotating member to rotate, on an inner side of the peripheral wall, and a through hole that extends through a portion of the peripheral wall and guides the infrared light that has passed through the first band pass filter or the second band pass filter toward the detector.

Accordingly, light from the outside of the gas concentration measurement device is further limited. Therefore, the measurement sensitivity of the gas concentration measurement device is further increased.

In a gas concentration measurement device according to a preferred embodiment of the present invention, the surrounding frame preferably includes a hole that receives the rotating shaft. In addition, the rotating member preferably includes an opposing wall that opposes the hole.

In this case, light from the outside of the gas concentration measurement device is further limited. Therefore, the measurement sensitivity is further increased.

In a gas concentration measurement device according to a preferred embodiment of the present invention, the surrounding frame preferably includes a first surrounding frame and a second surrounding frame that are separate members. In this case, the first surrounding frame preferably defines the rotation space at a side near the detector, and the second surrounding frame preferably defines the rotation space at a side near the light source. In addition, the through hole is preferably provided in the first surrounding frame, and the waveguide is preferably provided on the second surrounding frame.

In this case, the moldability of the surrounding frame is increased. Accordingly, the degree of design flexibility of the surrounding frame is increased.

In a gas concentration measurement device according to a preferred embodiment of the present invention, the rotating member includes another opposing wall that opposes a joining interface between the first surrounding frame and the second surrounding frame.

In this case, another component that limits light from the outside of the gas concentration measurement device is provided. Accordingly, the measurement sensitivity is further increased.

Preferably, a gas concentration measurement device according to a preferred embodiment of the present invention further includes a housing. In this case, the housing preferably contains a sample cell in which the rotating member is disposed and the rotational driver.

In this case, the gas concentration measurement device is able to be reduced in size, and the design freedom of the gas concentration measurement device is increased.

In a gas concentration measurement device according to a preferred embodiment of the present invention, the detector preferably includes a cavity through which the infrared light guided out of the through hole in the surrounding frame is guided toward the light-receiving portion. In addition, preferably, a projection of the through hole obtained when the through hole is projected toward the detector in an axial direction of the through hole does not overlap the cavity.

In this case, the risk that the infrared light that has passed through the through hole will be limited by the cavity is reduced and the amount of light received by the detector is increased. Accordingly, the measurement sensitivity is increased.

According to various preferred embodiments of the present invention, gas concentration measurement devices with significantly reduced sizes are provided.

The above and other elements, features, steps, characteristics and advantages of the present invention will become more apparent from the following detailed description of the preferred embodiments with reference to the attached drawings.

DETAILED DESCRIPTION OF THE PREFERRED EMBODIMENTS

Figure 1:
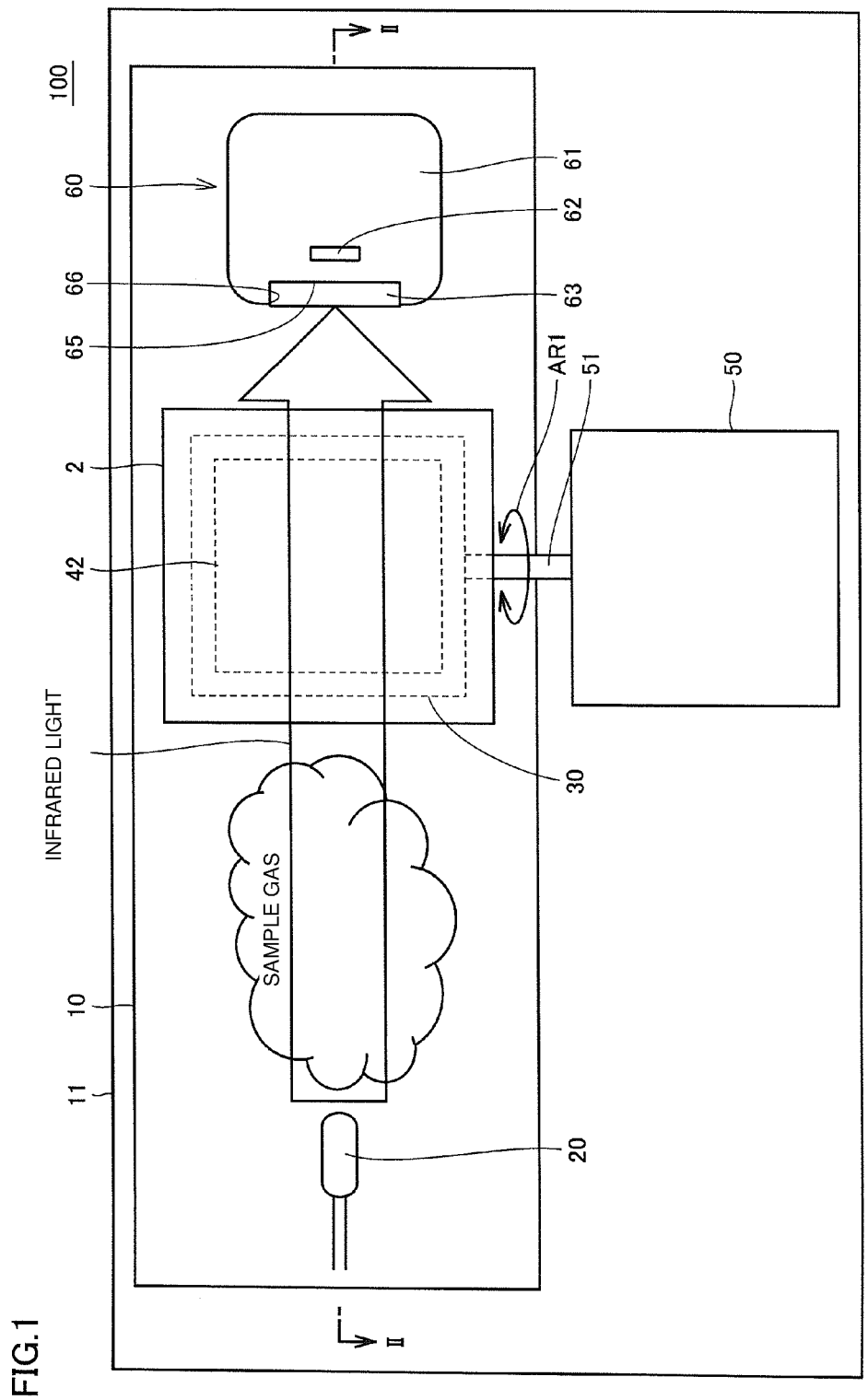
FIG. 1 is a top view of a gas concentration measurement device according to a first preferred embodiment of the present invention.

Preferred embodiments and modifications thereof according to the present invention will be described in detail with reference to the drawings. In the preferred embodiments and modifications thereof described below, components that are the same or similar are denoted by the same reference numerals in the drawings, and descriptions thereof will not be repeated.

First Preferred Embodiment

Figure 2:
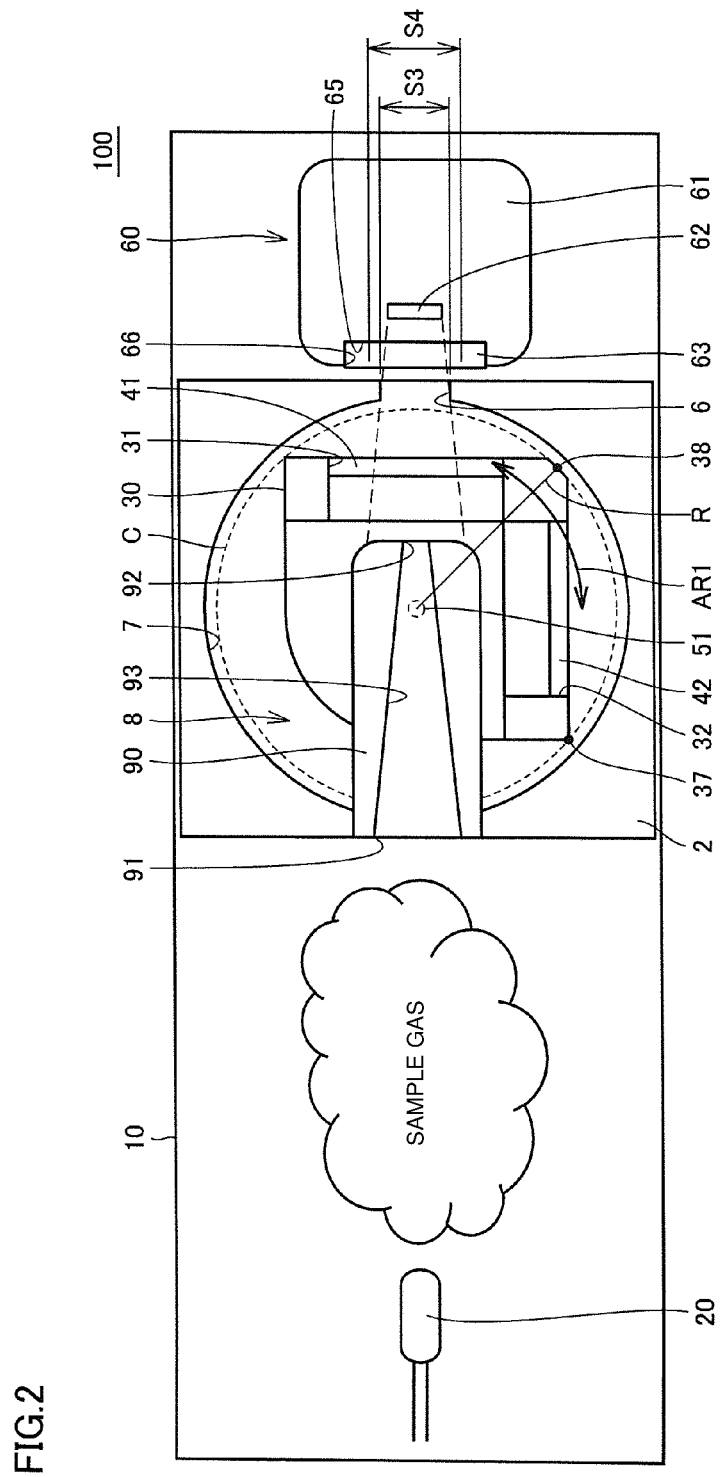
FIG. 2 is a sectional view taken along line II-II in FIG. 1, illustrating a first state of a rotating holder.
Figure 3:
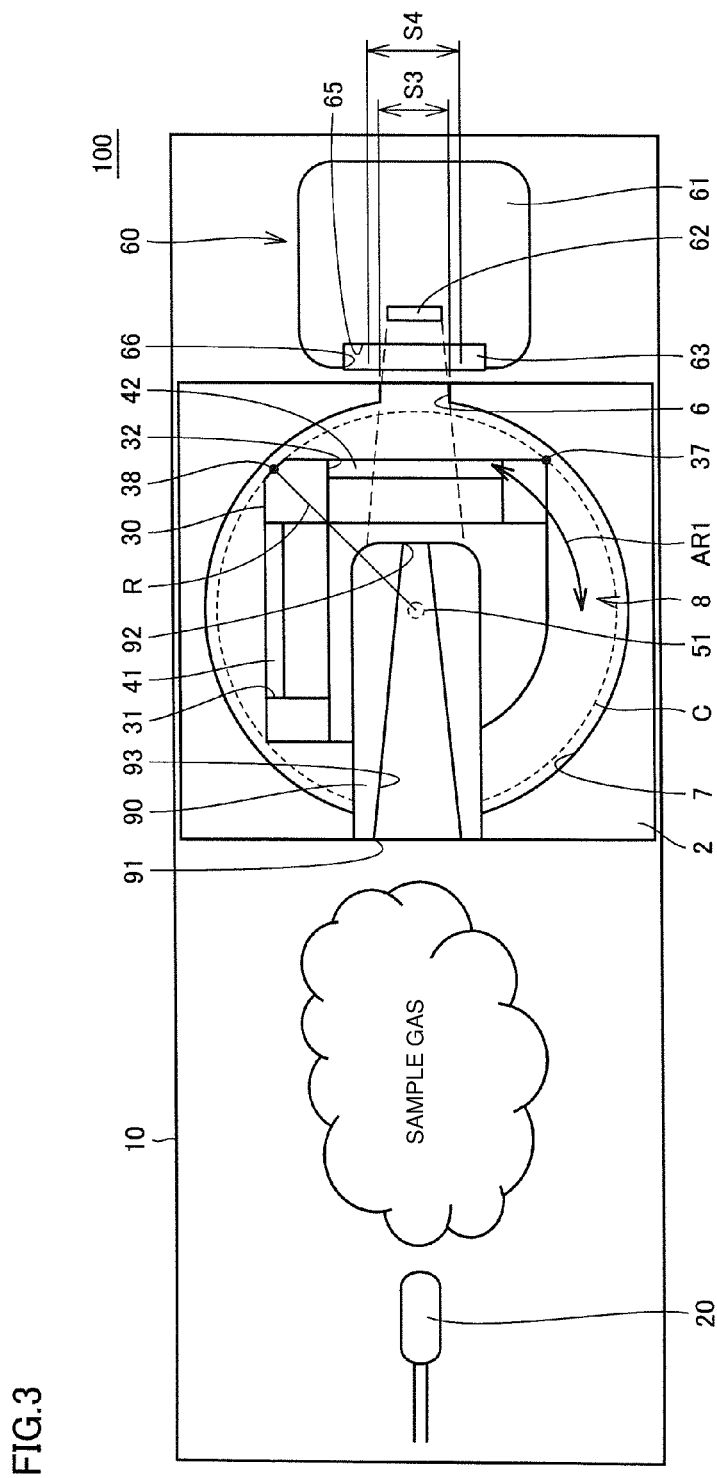
FIG. 3 is a sectional view taken along line II-II in FIG. 1, illustrating a second state of the rotating holder.
Figure 4:
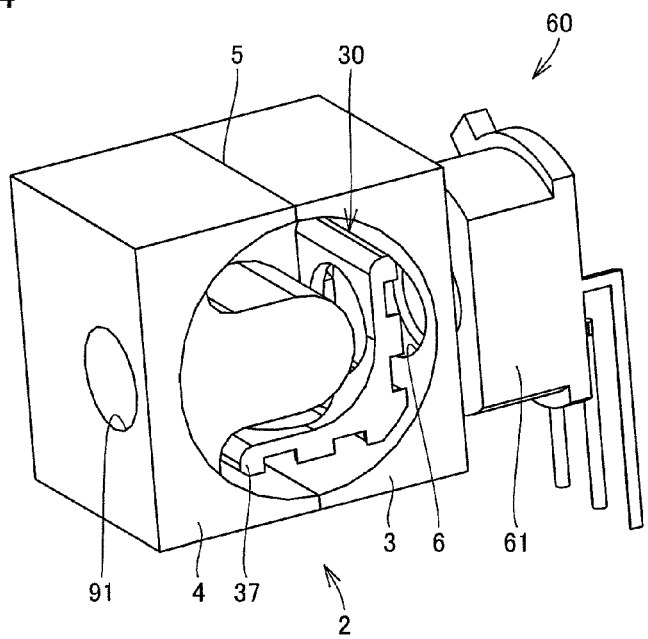
FIG. 4 is a sectional view taken at a first position of the structure to guide infrared light emitted from a light source toward a detector.

FIG. 1 is a top view of a gas concentration measurement device according to a first preferred embodiment of the present invention. FIGS. 2 and 3 are sectional views taken along line II-II in FIG. 1, illustrating a first state and a second state, respectively, of a rotating holder. The gas concentration measurement device according to the present preferred embodiment will be described with reference to FIGS. 1 to 3.

As illustrated in FIGS. 1 to 3, a gas concentration measurement device 100 according to the present preferred embodiment includes a housing 11 containing a sample cell 10 and a rotational driver 50. The gas concentration measurement device 100 also includes the sample cell 10, a light source 20, a rotating holder 30, a first band pass filter 41 (see FIG. 2), a second band pass filter 42, a detector 60, a surrounding frame 2, and a waveguide 90 (see FIG. 2). The rotating holder 30 corresponds to a "rotating member".

The gas concentration measurement device 100 measures a gas concentration in accordance with the absorbance of sample gas that flows through a space between the light source 20, which emits infrared light, and the detector 60, which includes a light-receiving portion 62 that receives the infrared light. As illustrated in FIGS. 4 to 7, the surrounding frame 2, the waveguide 90, and the rotating holder 30 correspond to a structure to guide the infrared light emitted from the light source to the detector.

The sample cell 10 includes a sample-gas flow space and allows the sample gas to flow therethrough. For example, a sample-gas introduction hole (not shown) is provided at one end of the sample cell 10 (end close to the light source 20 in FIG. 1), and a sample-gas discharge hole (not shown) is provided at the other end of the sample cell 10 (end close to the detector 60 in FIG. 1). The sample gas introduced into the sample cell 10 through the sample-gas introduction hole is discharged through the sample-gas discharge hole.

The sample cell 10 contains the light source 20, the waveguide 90, the rotating holder 30, and the detector 60. The light source 20, the waveguide 90, the rotating holder 30, and the detector 60 are arranged, for example, in that order from one end of the sample cell 10. The rotational driver 50 is disposed outside the sample cell 10. The sample cell 10 and the rotational driver 50 are disposed in the housing 10 so that the rotational driver 50 is not exposed. Thus, the design freedom of the gas concentration measurement device is increased. The sample cell 10 may be either defined as a portion of the housing 11 or formed separately from the housing 11.

The light source 20 emits infrared light. The light source 20 may be, for example, a filament lamp or an LED lamp that emits wide-band infrared light including desired infrared light. A portion of the infrared light emitted from the light source 20 is absorbed depending on infrared light absorption wavelength characteristics of the sample gas.

The waveguide 90 includes a wave-guiding portion 93 including a tubular inner peripheral surface; an entrance 91 one end of the wave-guiding portion 93 and through which the infrared light from the light source 20 is introduced; and an exit 92 at the other end of the wave-guiding portion 93 and guides the infrared light that has passed through the wave-guiding portion 93 toward the detector 60. The waveguide 90 guides the infrared light toward the detector 60 after a portion of the infrared light is absorbed by the sample gas.

The inner peripheral surface of the wave-guiding portion 93 includes a tapered region in which the cross-sectional area of the flow path decreases from the entrance 91 toward the exit 92. The tapered region has a truncated petrous shape whose circumference decreases from the entrance 91 toward the exit 92. The truncated petrous shape includes a truncated conical shape and a truncated polygonal pyramidal shape.

The waveguide 90 may be made of a resin material, such as acrylonitrile butadiene styrene copolymer synthetic resin (ABS resin) or polycarbonate resin (PC resin). In particular, the waveguide 90 is preferably made of a resin material having a reflectance of about 20% or less, for example.

The first band pass filter 41 and the second band pass filter 42 are provided on the rotating holder 30. The first band pass filter 41 and the second band pass filter 42 are located on a pair of planes 71 and 72 (see FIG. 9) that intersect each other. The rotating holder 30 is rotated around a predetermined rotating shaft 51, which will be described below, by the rotational driver 50, so that the first band pass filter 41 and the second band pass filter 42 are selectively disposed at a transmitting position, at which the infrared light guided out of the exit 92 of the waveguide 90 is transmitted toward the detector 60.

The first band pass filter 41 transmits the infrared light in an absorption band of the sample gas to be detected. Thus, only the infrared light having a desired wavelength band reaches the detector 60. The sample gas to be detected is, for example, carbon dioxide, and the absorption band thereof is about 4.3 μm.

The second band pass filter 42 transmits the infrared light in a wavelength band different from that of the infrared light transmitted by the first band pass filter 41. The second band pass filter 42 transmits, for example, the infrared light in an approximately 3.9 μm band, which is not absorbed by the sample gas.

In general, it is known that the output of the detector 60 drifts due to variations in the amount of infrared light from the light source 20 and the ambient temperature. In the present preferred embodiment, the second band pass filter 42 (band pass filter for reference light) and the first band pass filter 41 are switched to calculate the amount of change in the value of wavelength of the absorption band of the sample gas with respect to the value of wavelength at which the sample gas is not absorbed, so that the sensitivity is able to be corrected. Accordingly, the detection sensitivity of the detector 60 is able to be maintained constant for a long time.

The rotating holder 30 holds the first band pass filter 41 and the second band pass filter 42, and is rotatable around the rotating shaft 51 (in the direction denoted by AR1 in FIG. 1). The rotating holder 30 holds the first band pass filter and the second band pass filter 42 so that the first band pass filter 41 and the second band pass filter 42 are located on the planes 71 and 72 (see FIG. 9) that intersect each other. The rotating shaft 51 intersects the axial direction of the waveguide 90. More specifically, the rotating shaft 51 is parallel or substantially parallel to the pair of planes 71 and 72, intersecting each other, on which the first band pass filter 41 and the second band pass filter 42 are located.

The rotational driver 50 rotates the rotating holder around the rotating shaft 51 to switch between the first state (see FIG. 2), in which the first band pass filter 41 is at the above-described transmitting position, and the second state (see FIG. 3), in which the second band pass filter 42 is at the transmitting position. The rotating holder 30 includes a maximum radius portion 38 at which the radius of gyration R around the rotating shaft 51 is at a maximum. The detailed structure of the rotating holder 30 will be described below with reference to FIGS. 8 to 10.

The rotational driver 50 is connected to the rotating holder 30 by the rotating shaft 51. The rotating shaft 51 extends through a hole (not shown) in the sample cell. Thus, the rotating shaft 51 connects the rotating holder 30, which is contained in the sample cell 10, and the rotational driver 50, which is disposed outside the sample cell 10.

The rotational driver 50 rotates the rotating holder around the rotating shaft 51. The rotational driver 50 switches between the first state and the second state by rotating the rotating holder 30 around the rotating shaft 51 by approximately 90 degrees, for example.

The rotational driver 50 may be, for example, a stepping motor. In the case where a stepping motor is used, the position repeatability of the rotating holder 30 is increased when switching between the first state and the second state is performed. In addition, since the stepping motor exerts a holding torque without electricity, power consumption is able to be reduced.

The surrounding frame 2 surrounds the periphery of the rotating holder 30. The surrounding frame 2 has a rectangular or substantially rectangular parallelepiped shape in which a space is provided. The surrounding frame 2 includes a peripheral wall 7 and a through hole 6. The peripheral wall 7 defines a rotation space 8, which enables the rotating holder 30 to rotate therein, on the inner side thereof. The rotation space 8 is larger than a reference circle C, which indicates a rotation locus obtained when the maximum radius portion 38 of the rotating holder 30 is imaginarily rotated around the rotating shaft 51.

The waveguide 90 is disposed in the rotation space 8 of the surrounding frame 2 so as to extend toward the detector such that the waveguide 90 does not interfere with the rotation of the rotating holder 30. The waveguide 90 is preferably disposed near the first band pass filter 41 or the second band pass filter 42 that is located at the transmitting position. Accordingly, the exit 92 of the waveguide 90 is disposed in the reference circle C, which is the rotation locus obtained when the maximum radius portion 38 of the rotating holder 30 is imaginarily rotated around the rotating shaft 51.

When the exit 92 is disposed near the first band pass filter 41 or the second band pass filter 42 that is located at the transmitting position, the infrared light is incident on the first band pass filter 41 or the second band pass filter 42 at a small incident angle. Accordingly, the detection accuracy of the gas concentration measurement device is increased.

The through hole 6 extends through a portion of the peripheral wall 7, and guides the infrared light that has passed through the first band pass filter 41 or the second band pass filter 42 toward the detector 60. More specifically, the exit 92 of the waveguide 90, the first band pass filter 41 or the second band pass filter 42 that is located at the transmitting position, the through hole 6, and the light-receiving portion 62 of the detector 60 are aligned.

FIGS. 4 to 7 are sectional views taken at first to third positions of the structure to guide the infrared light emitted from the light source toward the detector and a perspective view of the structure to guide the infrared light emitted from the light source toward the detector. The second position is at or substantially at the center along the length of the surrounding frame 2 in a rotation axis direction. The first position is closer to the rotational driver than the second position, and the third position is closer to the rotational driver than the first position. The detailed structure of the surrounding frame 2 will be described with reference to FIGS. 4 to 7.

As illustrated in FIGS. 4 to 7, the surrounding frame 2 preferably includes a first surrounding frame 3 and a second surrounding frame 4 that are separate components. In this case, the surrounding frame 2 is formed preferably by joining the first surrounding frame 3 and the second surrounding frame 4 at a joining interface 5. When the first surrounding frame 3 and the second surrounding frame 4 are formed as separate components, the moldability of the surrounding frame 2 is increased. Accordingly, the degree of design flexibility of the surrounding frame 2 is increased.

The first surrounding frame 3 defines a portion of the rotation space 8 near the detector 60. The through hole 6 is provided in the first surrounding frame 3. The second surrounding frame 4 defines a portion of the rotation space 8 near the light source 20. The waveguide 90 is disposed in the second surrounding frame 4. The second surrounding frame 4 and the waveguide 90 are preferably formed integrally with each other by, for example, injection molding. The waveguide 90 may instead be formed by, for example, cutting.

The surrounding frame 2 includes a hole 9 through which the rotating shaft 51 extends (so that the rotating shaft 51 is able to be connected to the rotating holder 30). The hole 9 is located in a side portion of the surrounding frame 2 that faces the rotational driver 50.

Referring to FIGS. 2 and 3 again, the detector 60 may be an infrared light detector, such as a thermopile or a bolometer. The detector 60 includes a main portion 61, a light-receiving portion 62, and an optical window 63. The main portion is made of, for example, a metal, and the light-receiving portion 62 is embedded therein. The light-receiving portion 62 receives the infrared light guided out of the through hole 6 in the surrounding frame 2 through a cavity 66 and the optical window 63.

The optical window 63 is disposed in a recess 65 in a surface of the main portion 61 that faces the surrounding frame 2. The optical window 63 may be composed of, for example, a material that transmits infrared light, such as silicon or germanium, or a component obtained by forming an optical film, such as an antireflection film, on the material.

The positional relationship between the through hole 6 and the cavity 66 is such that the infrared light guided out of the through hole 6 passes through the cavity 66. More specifically, the positional relationship is such that the projection of the through hole 6 obtained when the through hole 6 is projected toward the detector 60 in the axial direction of the through hole 6 does not overlap the cavity 66. When the opening area of the through hole 6 is S3 and the area of a portion of the optical window 63 that is exposed at the cavity 66 is S4, S3 is smaller than S4. Accordingly, the infrared light guided out of the through hole 6 is able to be efficiently guided to the light-receiving portion 62.

The detector 60 is electrically connected to a signal processing circuit board (not shown). The detector 60 outputs an output signal to the signal processing circuit board based on the infrared light received by the light-receiving portion 62. The signal processing circuit board calculates the concentration of the sample gas based on the output signal.

Figure 8:
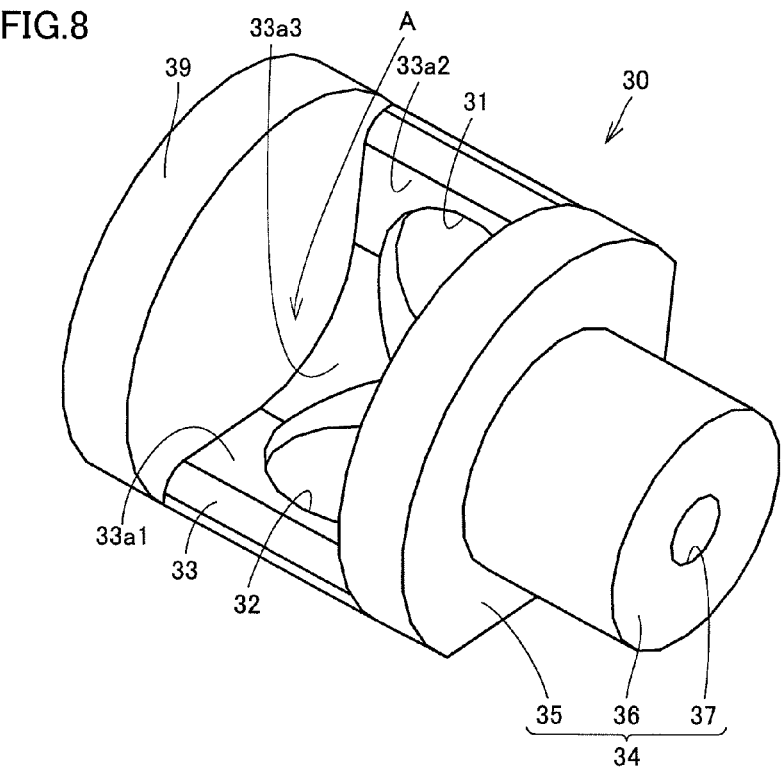
FIG. 8 is a schematic diagram of the rotating holder illustrated in FIG. 1.
Figure 9:
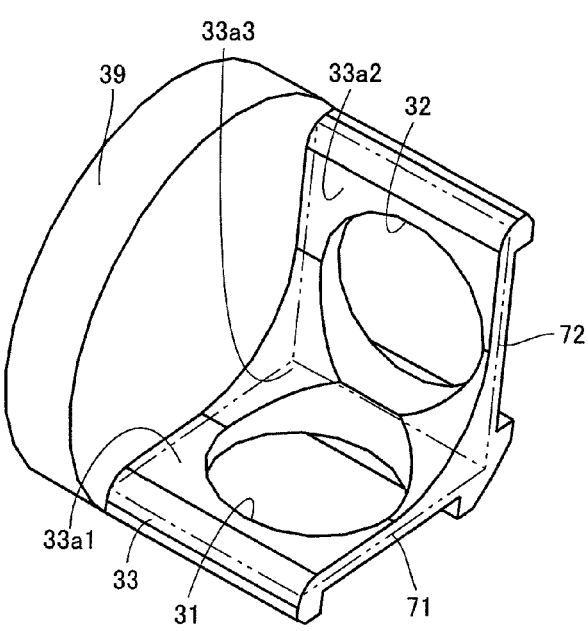
FIG. 9 is a schematic diagram of an opposing wall and a main portion of the rotating holder illustrated in FIG. 8.
Figure 10:
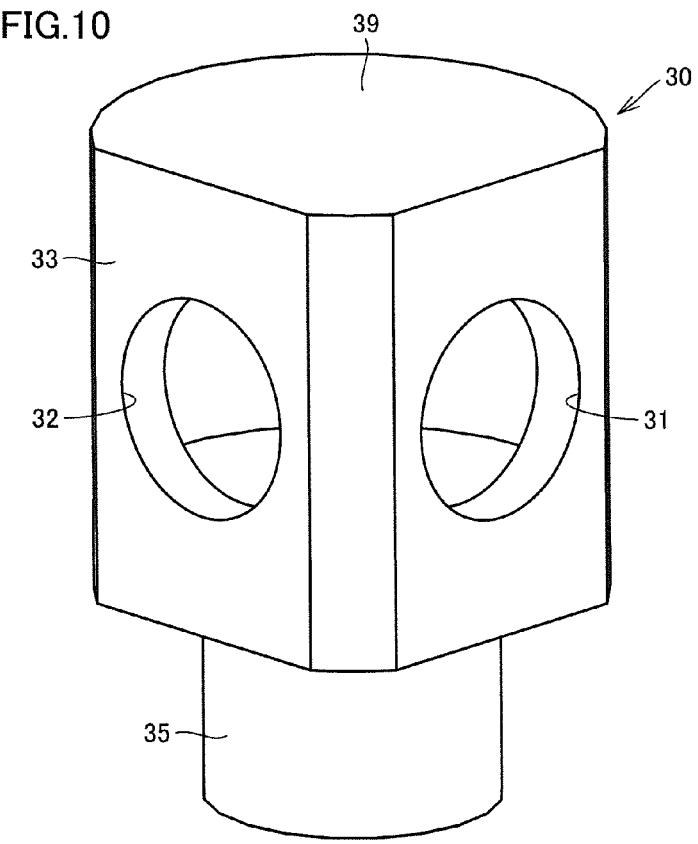
FIG. 10 is a schematic diagram illustrating outer side surfaces of the rotating holder illustrated in FIG. 8.

FIG. 8 is a schematic diagram of the rotating holder illustrated in FIG. 1. FIG. 9 is a schematic diagram of an opposing wall and a main portion of the rotating holder illustrated in FIG. 8. FIG. 10 is a schematic diagram illustrating outer side surfaces of the rotating holder illustrated in FIG. 8. The shape of the rotating holder 30 will be described in detail with reference to FIGS. 8 to 10.

As illustrated in FIGS. 8 to 10, the rotating holder includes a main portion 33, an opposing wall 35, another opposing wall 39, and a rotating-shaft-receiving portion 36. The main portion 33 is L-shaped or substantially L-shaped. The main portion 33 is a portion that holds the first band pass filter 41 and the second band pass filter 42. The main portion 33 includes a first through hole 31 to which the first band pass filter 41 is securely fitted and a second through hole 32 to which the second band pass filter 42 is securely fitted.

The inner peripheral surface of the main portion 33 includes a first flat portion 33a1, a second flat portion 33a2, and a connecting portion 33a3. The first flat portion 33a1 is flat and faces the detector 60 when the first band pass filter 41 is located at the transmitting position.

The second flat portion 33a2 is flat and is parallel or substantially parallel to the axial direction of the rotating shaft 51 and the direction in which the waveguide 90 and the detector 60 are arranged when the first band pass filter 41 is located at the transmitting position. The second flat portion 33a2 is closer to the light source 20 than the first flat portion 33a1 is when the first band pass filter 41 is located at the transmitting position.

The connecting portion 33a3 connects the first flat portion 33a1 and the second flat portion 33a2 to each other. The connecting portion 33a3 is curved so as to approach the second flat portion 33a2 along the direction perpendicular or substantially perpendicular to the axial direction of the rotating shaft 51 and the direction in which the waveguide 90 and the detector 60 are arranged when the first band pass filter 41 is located at the transmitting position.

In the state in which the first band pass filter 41 is located at the transmitting position, the length of the main portion 33 in the direction in which the waveguide 90 and the detector 60 are arranged is the same or substantially the same as the length of the main portion 33 in the direction perpendicular or substantially perpendicular to the axial direction of the rotating shaft 51 and the direction in which the waveguide 90 and the detector 60 are arranged.

The first band pass filter 41, which is fitted to the first through hole 31, is located on the first plane 71. The second band pass filter 42, which is fitted to the second through hole 32, is located on the second plane 72. The first plane 71 and the second plane 72 are perpendicular or substantially perpendicular to each other. The relationship in which the first plane 71 and the second plane 72 are perpendicular or substantially perpendicular to each other means that the crossing angle θ between the first plane 71 and the second plane 72 is in the range of about 85 degrees to about 95 degrees, for example. Thus, a case in which the crossing angle between the first plane 71 and the second plane 72 differs from 90 degrees due to design errors is included.

The opposing wall 35 and the other opposing wall 39 are, for example, fan-shaped. The opposing wall 35 and the other opposing wall 39 are arranged so as not to oppose the first through hole 31 and the second through hole 32 and such that the main portion 33 is interposed therebetween. The opposing wall 35 and the opposing wall 39 are arranged in the rotation axis direction. The opposing wall 35 and the other opposing wall 39 are provided at the end portions of the main portion 33 in the rotation axis direction.

The rotating-shaft-receiving portion 36 projects from the opposing wall 35 toward the rotational driver 50 (see FIG. 1). The rotating-shaft-receiving portion 36 is cylindrical or substantially cylindrical, and includes a receiving hole 37 that receives the rotating shaft 51. The rotating shaft 51 is inserted into the receiving hole 37 and fixed to the receiving hole 37 so that the rotating holder 30 rotates together with the rotating shaft 51.

The opposing wall 35, the other opposing wall 39, and the main portion 33 define an open space A that opens in the axial direction of the first through hole 31 and the axial direction of the second through hole 32. The above-described waveguide 90 is disposed in the open space A. Accordingly, the waveguide 90 does not interfere with the rotating holder 30 when the rotating holder 30 is rotated.

The hole 9 in the above-described surrounding frame 2 enables the rotating-shaft-receiving portion 36 to be inserted therein. The opposing wall 35 opposes the hole 9 to prevent infrared light from entering through the hole 9. To prevent infrared light from entering along the joining interface between the first surrounding frame 3 and the second surrounding frame 4 at a side portion of the surrounding frame 2 that opposes the side portion in which the hole 9 is formed, the other opposing wall 39 opposes the joining interface. Light from the outside of the gas concentration measurement device is further limited by arranging the opposing wall 35 and the other opposing wall 39 in the above-described manner. Accordingly, the measurement sensitivity is further increased.

In addition, since the distance between the exit of the waveguide and the band pass filters retained by the rotating holder is able to be reduced, the irradiation efficiency is increased. Accordingly, the measurement sensitivity is increased.

Figure 5:
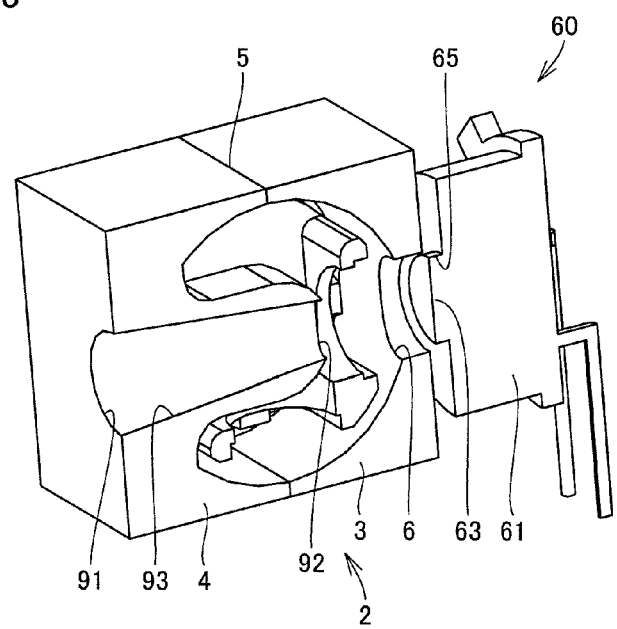
FIG. 5 is a sectional view taken at a second position of the structure to guide the infrared light emitted from the light source toward the detector.
Figure 6:
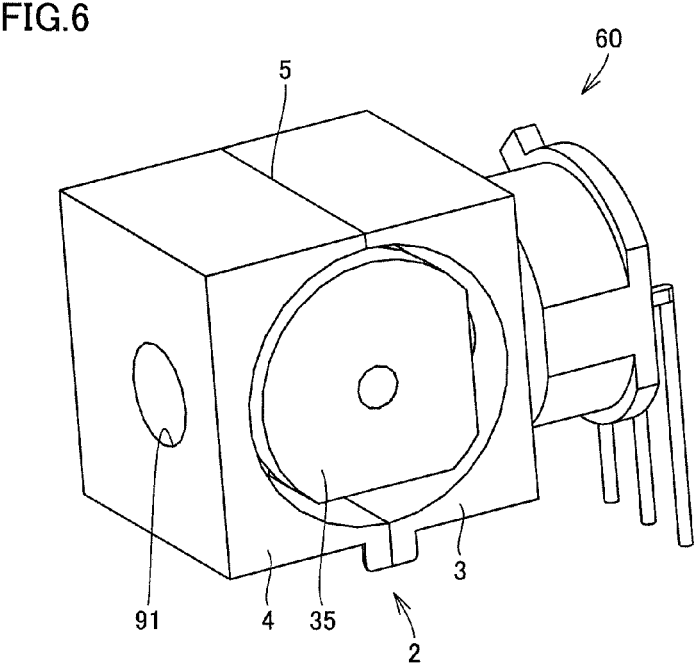
FIG. 6 is a sectional view taken at a third position of the structure to guide the infrared light emitted from the light source toward the detector.
Figure 7:
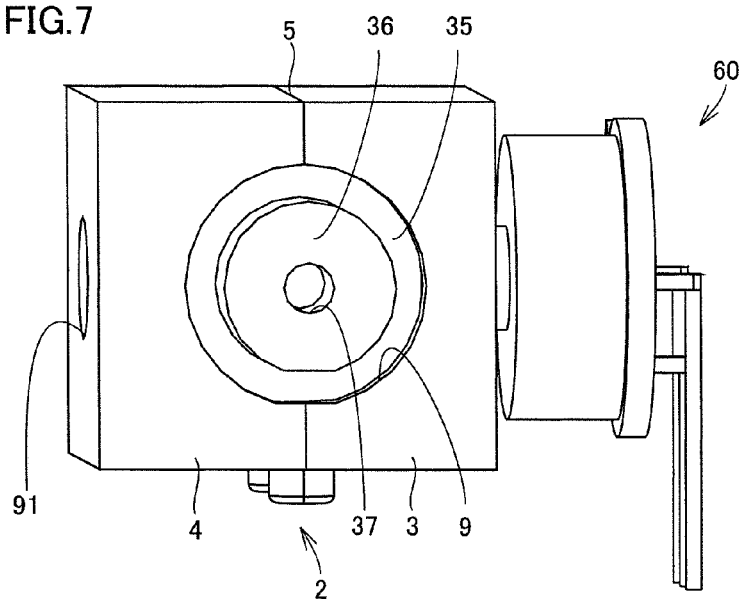
FIG. 7 is a perspective view of the structure to guide the infrared light emitted from the light source toward the detector.
Figure 11:
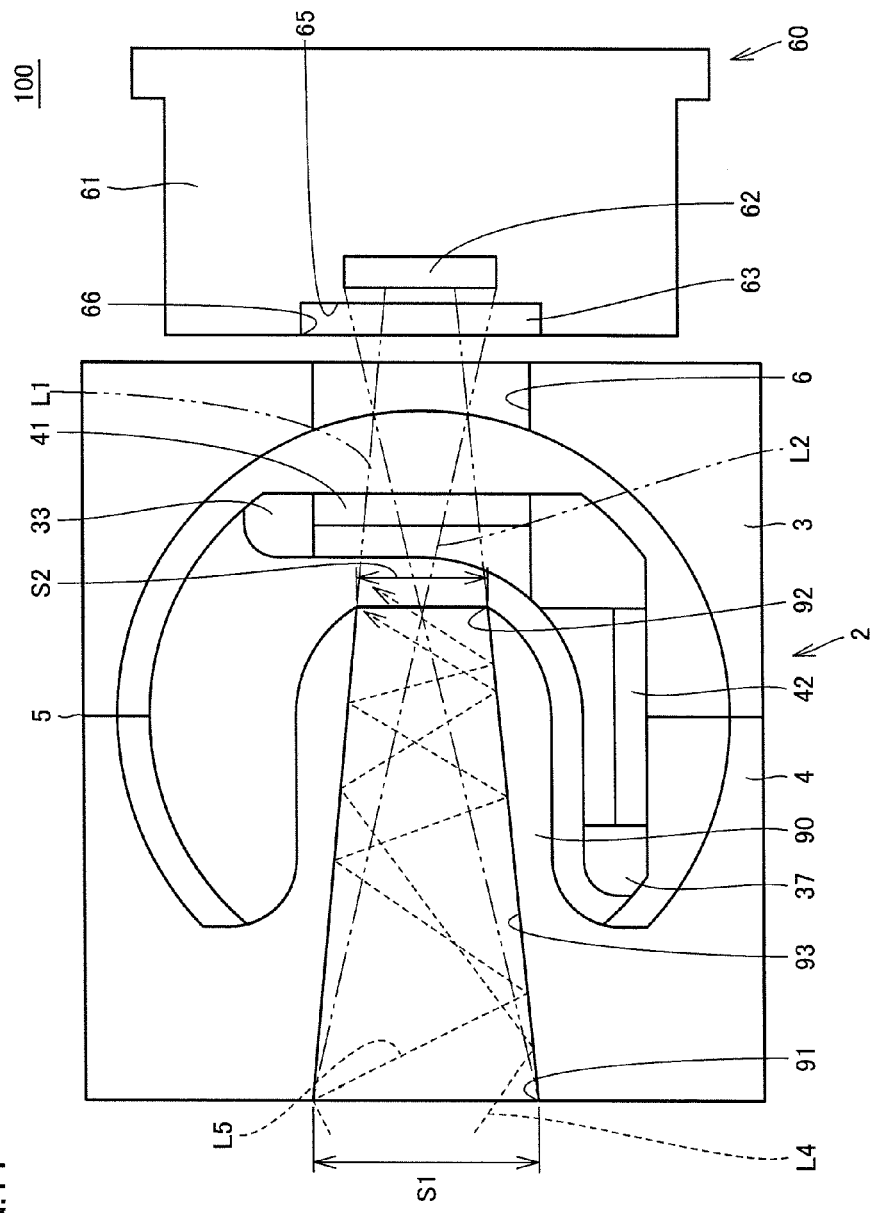
FIG. 11 illustrates infrared light that travels through a waveguide illustrated in FIG. 5.

FIG. 11 illustrates infrared light that travels through the waveguide illustrated in FIG. 5. The infrared light that travels through the waveguide 90 will be described with reference to FIG. 11.

Referring to FIG. 11, the infrared light that linearly travels through the region that is the logical sum of the region surrounded by the outermost rays of infrared light L1 and the region surrounded by the outermost rays of infrared light L2 mainly reaches the light-receiving portion 62. The infrared light L1 is light having a truncated petrous shape that linearly travels along the peripheral surface of the wave-guiding portion 93 toward the detector 60. The infrared light L2 is light having a shape including two truncated cones obtained by rotating, for example, a ray of light that linearly travels from the bottom end of the entrance 91 of the waveguide 90 in FIG. 11 to the top end of the light-receiving portion 62 in FIG. 11, one turn along the opening shape of the entrance 91.

The infrared light that linearly travels through the region that is the logical sum of the region surrounded by the outermost rays of the infrared light L1 and the region surrounded by the outermost rays of the infrared light L2 passes through the first band pass filter 41 or the second band pass filter 42 that is located at the transmitting position at a relatively small angle.

In general, the transmission bands of the first band pass filter 41 and the second band pass filter 42 shift toward the short-wavelength side as the incident angle increases. The measurement accuracy decreases when the transmission bands vary. Therefore, when the measurement is performed, the incident angle of the infrared light incident on the first band pass filter 41 and the second band pass filter 42 is preferably small.

In the present preferred embodiment, the waveguide 90 is provided to significantly reduce or prevent the influence on the measurement accuracy of the infrared light that is incident on the first band pass filter 41 or the second band pass filter that is located at the transmitting position at a large incident angle.

Infrared light L4 and infrared light L5 enter the wave-guiding portion 93 through the entrance 91 at a relatively large angle with respect to the axial direction of the wave-guiding portion 93. The infrared light L4 and the infrared light L5 travel toward the detector 60 while being reflected by the inner peripheral surface of the wave-guiding portion 93 a plurality of times.

If it is assumed that the reflectance of the wave-guiding portion 93 is 100%, the infrared light L4 and the infrared light L5 may be incident on the first band pass filter or the second band pass filter 42 that is located at the transmitting position at a large incident angle.

In the present preferred embodiment, the waveguide 90 is made of a resin material having a reflectance of about 20% or less, for example. Therefore, the infrared light L4 and the infrared light L5 are absorbed and attenuated by being repeatedly reflected in the wave-guiding portion 93. For example, in the case where the reflectance of the material is about 10%, the attenuation effect obtained when the infrared light is reflected five times is similar to that obtained when the infrared light is reflected once by a component having a reflectance of about 0.001%, for example. The number of times the infrared light L4 and the infrared light L5 are reflected is increased by setting an opening area S1 of the entrance 91 of the waveguide 90 greater than an opening area S2 of the exit 92 and forming the wave-guiding portion 93 so that the wave-guiding portion 93 includes a tapered region.

Thus, the waveguide 90 reflects the infrared light that has entered the wave-guiding portion 93 through the entrance 91 in the tapered region, thus reducing the energy of the infrared light that is obliquely incident on the first band pass filter 41 or the second band pass filter 42 that is located at the transmitting position. Accordingly, the measurement accuracy of the gas concentration measurement device is increased.

As described above, in the gas concentration measurement device 100 according to the present preferred embodiment, the rotating holder 30 holds the first band pass filter 41 and the second band pass filter 42 in such a manner that the first band pass filter 41 and the second band pass filter 42 are located on planes that intersect each other. Switching between the first state, in which the first band pass filter 41 is located at the transmitting position, and the second state, in which the second band pass filter 42 is located at the transmitting position, is performed by rotating the rotating holder 30 around the rotating shaft that intersects the axial direction of the waveguide 90. Accordingly, the gas concentration measurement device 100 is able to be reduced in size.

In addition, in the gas concentration measurement device 100 according to the present preferred embodiment, since the waveguide 90 is provided, the energy of the obliquely incident infrared light is able to be reduced. Therefore, the measurement accuracy of the gas concentration measurement device 100 is increased.

In the gas concentration measurement device 100 according to the present preferred embodiment, the inner periphery of the wave-guiding portion 93 of the waveguide 90 preferably has a petrous shape, for example. However, the shape of the inner periphery of the wave-guiding portion 93 is not limited to this, and may instead be cylindrical. Also in this case, the waveguide 90 may be disposed near the first band pass filter 41 or the second band pass filter 42 that is located at the transmitting position. Therefore, the amount of infrared light incident on the first band pass filter 41 or the second band pass filter 42 at a large incident angle is able to be considerably reduced.

First Modification

Figure 12:
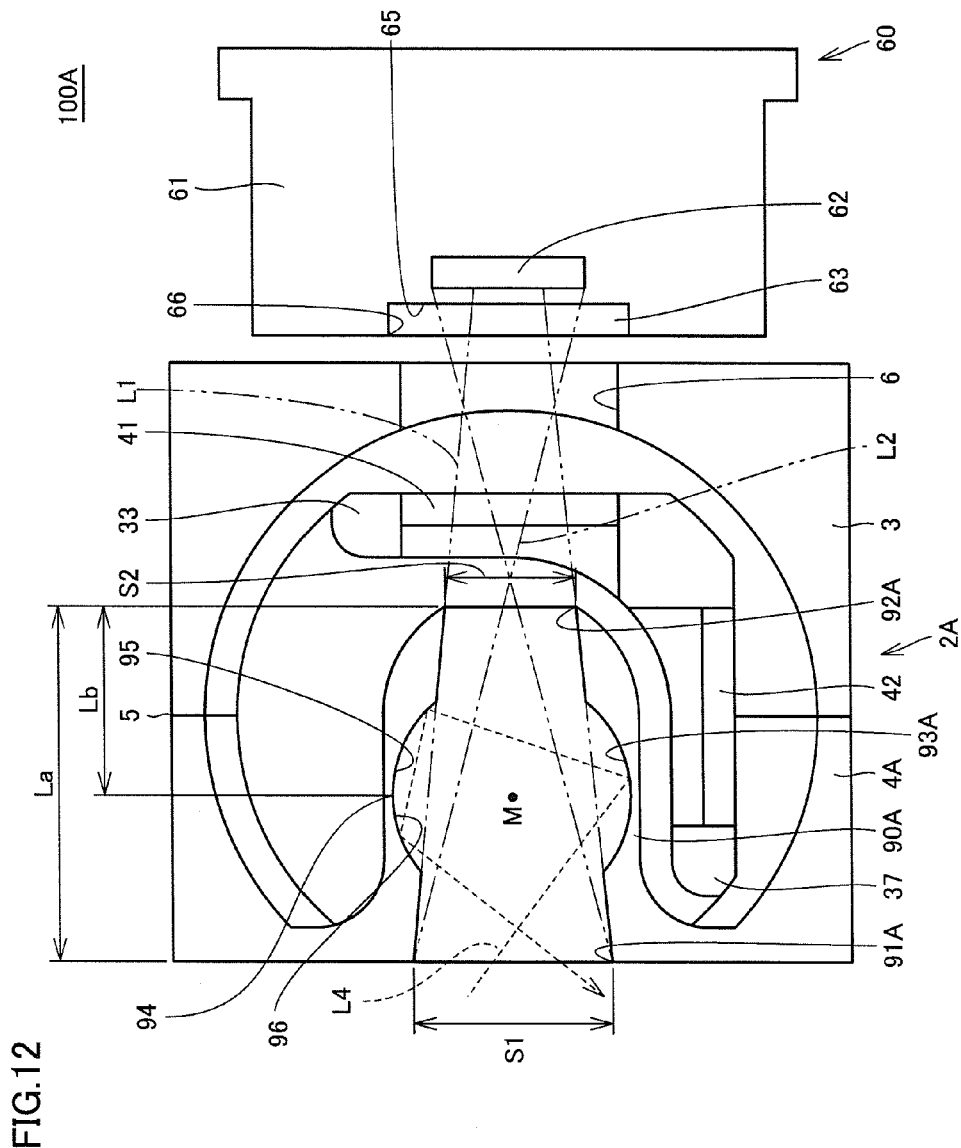
FIG. 12 illustrates infrared light that travels through a waveguide according to a first modification of a preferred embodiment of the present invention.

FIG. 12 illustrates infrared light that travels through a waveguide according to a first modification of a preferred embodiment of the present invention. A gas concentration measurement device 100A according to the first modification will be described with reference to FIG. 12.

As illustrated in FIG. 12, the gas concentration measurement device 100A according to the first modification includes a waveguide 90A including a wave-guiding portion 93A having a shape that differs from that in the gas concentration measurement device 100 according to the first preferred embodiment. Other structures are substantially the same as those in the first preferred embodiment.

Also in the waveguide 90A, the opening area of an entrance 91A is greater than the opening area of an exit 92A. The internal shape of the wave-guiding portion 93A is partially spherical. A portion of the inner peripheral surface of the wave-guiding portion 93A that defines a portion of a spherical surface is located between the entrance 91A and the exit 92A. The portion that defines a portion of a spherical surface includes a first spherical surface portion 95, which extends toward the exit 92A from a boundary at the center M of the sphere, and a second spherical surface portion 96, which extends toward the entrance 91A from the boundary at the center M. The region from the first spherical surface portion 95 to the exit 92 corresponds to a tapered region in which the cross-sectional area of the flow path decreases along the direction from the entrance 91A to the exit 92A, and also corresponds to a first curved portion having a circumference that decreases along the direction from the entrance 91A to the exit 92A. The second spherical surface portion 96 corresponds to a second curved portion having a circumference that decreases along the direction from the exit 92A to the entrance 91A.

Also when the wave-guiding portion 93A has the above-described shape, the infrared light that linearly travels through the region that is the logical sum of the region surrounded by the outermost rays of infrared light L1 and the region surrounded by the outermost rays of infrared light L2 mainly reaches the light-receiving portion 62.

A portion of infrared light L4 that has entered the wave-guiding portion 93 through the entrance 91A at a relatively large angle with respect to the axial direction of the wave-guiding portion 93A is reflected by the first spherical surface portion 95 and the second spherical surface portion 96 a plurality of times and is emitted from the entrance 91A. The remaining portion of the infrared light L4 that has entered the wave-guiding portion 93 through the entrance 91A at a relatively large angle with respect to the axial direction of the wave-guiding portion 93A travels toward the detector 60 while being reflected by the inner peripheral surface of the wave-guiding portion 93 a plurality of times.

The portion of the infrared light L4 that has been emitted from the entrance 91A is not incident on the first band pass filter 41 or the second band pass filter 42 that is located at the transmitting position. The portion of the infrared light L4 that travels toward the detector 60 while being reflected by the inner peripheral surface of the wave-guiding portion 93A a plurality of times is attenuated by the wave-guiding portion 93A. To increase the number of times the light is reflected by the wave-guiding portion 93A, the distance Lb from the first spherical surface portion 95 to the exit 92 in the axial direction of the wave-guiding portion 93A is preferably greater than or equal to half the length La of the waveguide 90.

Thus, in the present modification, the energy of the infrared light that is obliquely incident on the first band pass filter 41 or the second band pass filter 42 that is located at the transmitting position is able to be reduced, and a portion of the obliquely incident infrared light is able to be emitted from the entrance 91A. Accordingly, the measurement accuracy of the gas concentration measurement device 100A is further increased.

As described above, the gas concentration measurement device 100A according to the present modification is able to be reduced in size as in the first preferred embodiment, and the measurement accuracy thereof is further increased.

Second Modification

Figure 13:
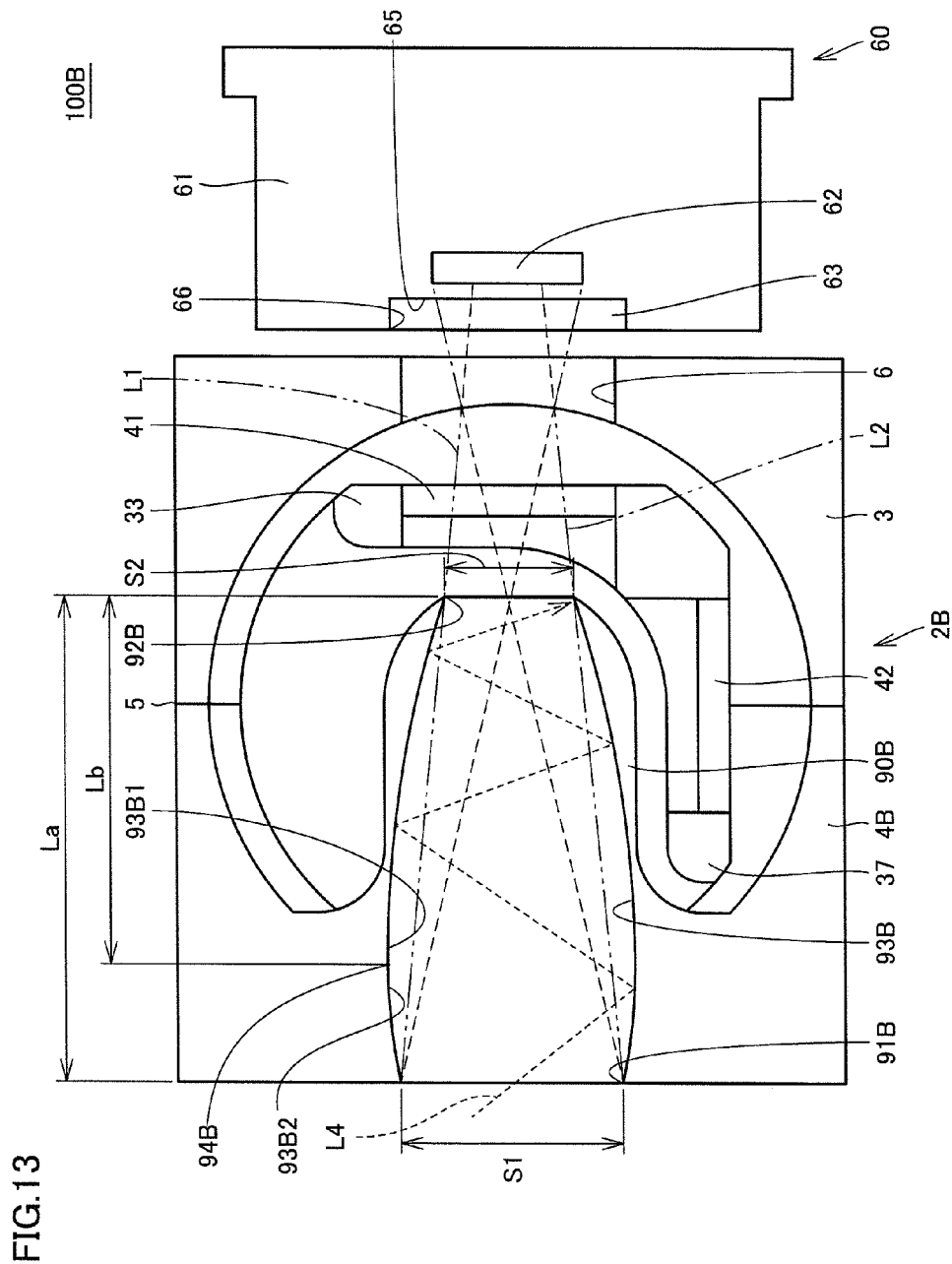
FIG. 13 illustrates infrared light that travels through a waveguide according to a second modification of a preferred embodiment of the present invention.

FIG. 13 illustrates infrared light that travels through a waveguide according to a second modification of a preferred embodiment of the present invention. A gas concentration measurement device 100B according to the second modification will be described with reference to FIG. 13.

As illustrated in FIG. 13, the gas concentration measurement device 100B according to the second modification includes a waveguide 90B including a wave-guiding portion 93B having a shape that differs from that in the gas concentration measurement device 100 according to the first preferred embodiment. Other structures are substantially the same as those in the first preferred embodiment.

Also in the waveguide 90B, the opening area of an entrance 91B is greater than the opening area of an exit 92B. The internal shape of the wave-guiding portion 93B includes a first curved portion 93B1 and a second curved portion 93B2. The wave-guiding portion 93B includes a maximum circumference portion 94B. The maximum circumference portion 94B is located between the entrance 91B and the exit 92B.

The first curved portion 93B1 defines the internal shape of the wave-guiding portion 93B in a region from the maximum circumference portion 94B to the exit 92B. The first curved portion 93B1 has a circumference that decreases along the direction from the entrance 91B to the exit 92B.

The second curved portion 93B2 defines the internal shape of the wave-guiding portion 93B in a region from the maximum circumference portion 94B to the entrance 91B. The second curved portion 93B2 has a circumference that decreases along the direction from the exit 92B to the entrance 91B.

Also in this case, the infrared light that linearly travels through the region that is the logical sum of the region surrounded by the outermost rays of infrared light L1 and the region surrounded by the outermost rays of infrared light L2 mainly reaches the light-receiving portion 62.

The length Lb of the first curved portion 93B1 in the axial direction of the waveguide 90B is preferably greater than or equal to half the length La of the waveguide 90B in the axial direction. When this length relationship is satisfied, infrared light L4, which enters through the entrance 91B at a relatively large angle with respect to the axial direction of the wave-guiding portion 93B, is reflected a plurality of times in the second curved portion 93B2.

Accordingly, also in the present modification, the energy of the infrared light that is obliquely incident on the first band pass filter 41 or the second band pass filter 42 that is located at the transmitting position is able to be reliably reduced. As a result, the measurement accuracy of the gas concentration measurement device 100B is increased.

As described above, similar to the first preferred embodiment, the gas concentration measurement device 100B according to the present modification includes a rotating holder 30, and therefore the size thereof is able to be reduced. In addition, the gas concentration measurement device 100B includes the waveguide 90B, and therefore the measurement accuracy thereof is increased.

Third Modification

Figure 14:
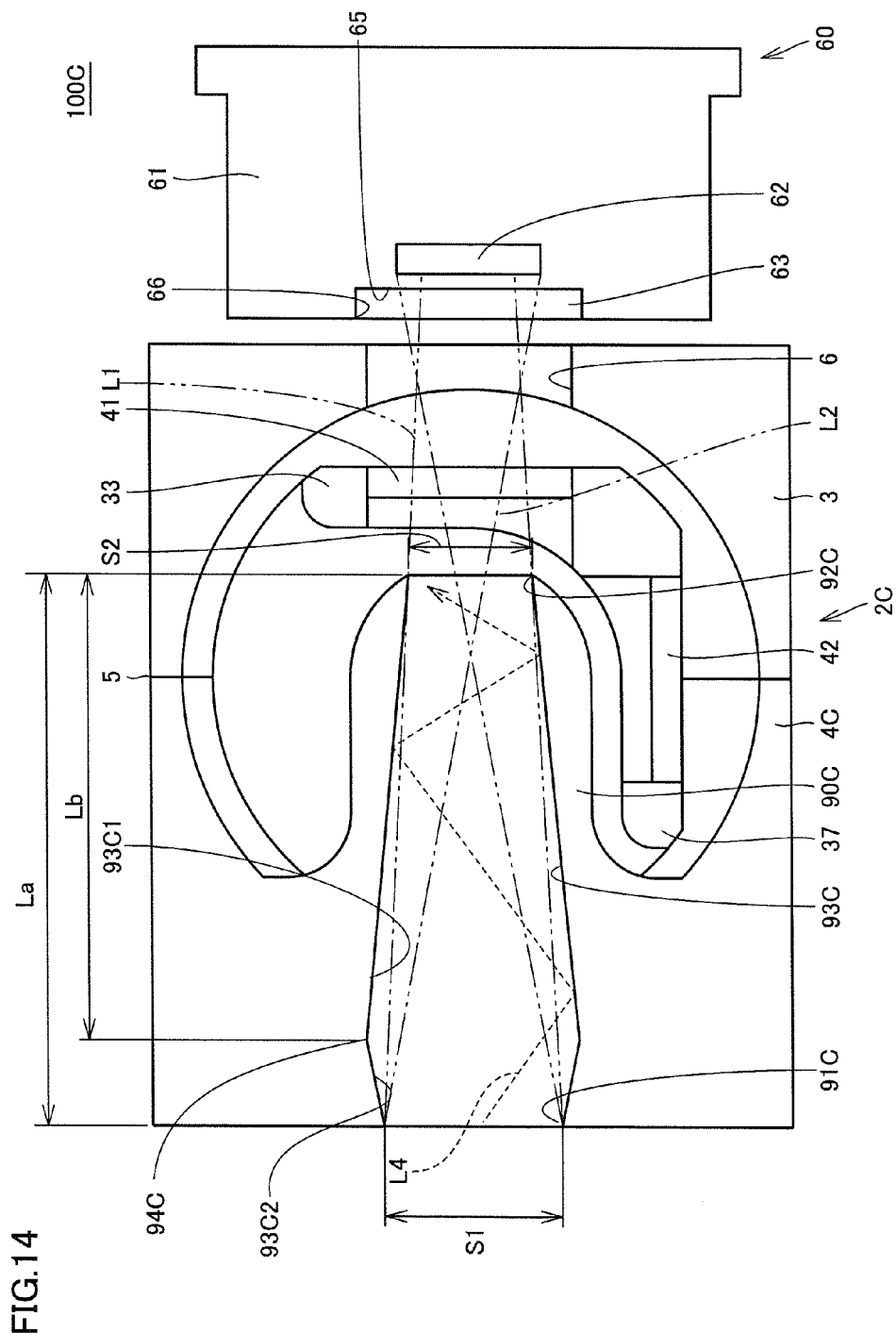
FIG. 14 illustrates infrared light that travels through a waveguide according to a third modification of a preferred embodiment of the present invention.

FIG. 14 illustrates infrared light that travels through a waveguide according to a third modification of a preferred embodiment of the present invention. A gas concentration measurement device 100C according to the third modification will be described with reference to FIG. 14.

As illustrated in FIG. 14, the gas concentration measurement device 100C according to the third modification includes a waveguide 90C including a wave-guiding portion 93C having a shape that differs from that in the gas concentration measurement device 100 according to the first preferred embodiment. Other structures are substantially the same as those in the first preferred embodiment.

Also in the waveguide 90C, the opening area of an entrance 91C is greater than the opening area of an exit 92C. The internal shape of the wave-guiding portion 93C includes a first truncated conical or pyramidal portion 93C1 and a second truncated conical or pyramidal portion 93C2. The wave-guiding portion 93C includes a maximum circumference portion 94C. The maximum circumference portion 94C is located between the entrance 91C and the exit 92C.

The first truncated conical or pyramidal portion 93C1 defines the internal shape of the wave-guiding portion 93C in a region from the maximum circumference portion 94C to the exit 92C. The first truncated conical or pyramidal portion 93C1 has a circumference that decreases along the direction from the entrance 91C to the exit 92C.

The second truncated conical or pyramidal portion 93C2 defines the internal shape of the wave-guiding portion 93C in a region from the maximum circumference portion 94C to the entrance 91C. The second truncated conical or pyramidal portion 93C2 has a circumference that decreases along the direction from the exit 92C to the entrance 91C.

Also in this case, the infrared light that linearly travels through the region that is the logical sum of the region surrounded by the outermost rays of infrared light L1 and the region surrounded by the outermost rays of infrared light L2 mainly reaches the light-receiving portion 62.

The length Lb of the first truncated conical or pyramidal portion 93C1 in the axial direction of the waveguide 90C is preferably greater than or equal to half the length La of the waveguide 90C in the axial direction. When this length relationship is satisfied, infrared light L4, which enters through the entrance 91C at a relatively large angle with respect to the axial direction of the wave-guiding portion 93C, is reflected a plurality of times in the second truncated conical or pyramidal portion 93C2.

Accordingly, also in the present modification, the energy of the infrared light that is obliquely incident on the first band pass filter 41 or the second band pass filter 42 that is located at the transmitting position is able to be reliably reduced. As a result, the measurement accuracy of the gas concentration measurement device is increased.

Although the sample gas is carbon dioxide in the present modification, the sample gas is not limited to this, and may instead be, for example, carbon monoxide, $CH_4$, or NOR.

As described above, similar to the first preferred embodiment, the gas concentration measurement device 100C according to the present modification includes a rotating holder 30, and therefore the size thereof is able to be reduced. In addition, the gas concentration measurement device 100C includes the waveguide 90C, and therefore the measurement accuracy thereof is increased.

In the above-described first preferred embodiment and first to third modifications, the first band pass filter 41 and the second band pass filter 42 are respectively fitted to the first through hole 31 and the second through hole 32 formed in the rotating holder 30. However, in the case where the main portion 31 of the rotating member 30 includes only the L-shaped or substantially L-shaped connecting portion 33a3 in the state illustrated in FIG. 8, the first band pass filter 41 and the second band pass filter 42 may instead be fixed so as to project from an end portion of the connecting portion 33a3 in the direction in which the waveguide and the detector are arranged and from an end portion of the connecting portion 33a in the direction perpendicular to the axial direction of the rotating shaft 51 and the direction in which the waveguide 90 and the detector 60 are arranged. In this case, at least one of the rotating member, an end portion of the first band pass filter 41, and an end portion of the second band pass filter 42 defines and functions as a portion at which the radius of gyration R around the rotating shaft 51 is at a maximum, that is, the maximum radius portion.

Although preferred embodiments and modifications thereof according to the present invention has been described, the preferred embodiments and modifications disclosed herein are illustrative and not restrictive in all points. The scope of the present invention is to be defined by the scope of the claims, and includes equivalents to the scope of the claims and all changes within the scope of the claims.

While preferred embodiments of the present invention have been described above, it is to be understood that variations and modifications will be apparent to those skilled in the art without departing from the scope and spirit of the present invention. The scope of the present invention, therefore, is to be determined solely by the following claims.

What is claimed is:

1. A gas concentration measurement device that measures a gas concentration based on an absorbance of sample gas in a region between a light source that emits infrared light and a detector that receives the infrared light, the gas concentration measurement device comprising:
    a waveguide including a wave-guiding portion including a tubular inner peripheral surface, an entrance at one side of the wave-guiding portion and through which the infrared light from the light source is introduced, and an exit at the other side of the wave-guiding portion and guiding the infrared light that has passed through the wave-guiding portion toward the detector;
    a rotating member that is rotatable around a rotating shaft that intersects an axial direction of the waveguide;
    a first band pass filter and a second band pass filter that are provided on the rotating member and located on a pair of planes that intersect each other;
    a rotational driver that rotates the rotating member around the rotating shaft; wherein
    the rotating member is rotated by the rotational driver so that the first band pass filter and the second band pass filter rotate around the wave guide and are selectively located at a transmitting position at which the infrared light guided out of the exit is transmitted toward the detector; and
    when a portion of the rotating member, the first band pass filter, or the second band pass filter, the portion having a maximum radius of gyration around the rotating shaft.

2. The gas concentration measurement device according to claim 1, wherein, when an end portion of the rotating member that is farthest from the detector in a state in which the first band pass filter is located at the transmitting position is defined as a distal end portion, the exit is closer to the detector than the distal end portion.

3. The gas concentration measurement device according to claim 1, wherein
    a portion or an entirety of an inner peripheral surface of the wave-guiding portion includes a tapered region including a cross section that decreases along a direction from the entrance to the exit; and
    the waveguide reflects the infrared light that has entered the wave-guiding portion through the entrance in the tapered region, so that energy of the infrared light that is obliquely incident on the first band pass filter or the second band pass filter that is located at the transmitting position is reduced.

4. The gas concentration measurement device according to claim 3, wherein the tapered region has a truncated petrous shape or a cylindrical shape.

5. The gas concentration measurement device according to claim 1, further comprising a surrounding frame that surrounds a periphery of the rotating member.

6. The gas concentration measurement device according to claim 5, wherein the surrounding frame includes:
    a peripheral wall that defines a rotation space, which enables the rotating member to rotate, on an inner side of the peripheral wall; and
    a through hole that extends through a portion of the peripheral wall and guides the infrared light that has passed through the first band pass filter or the second band pass filter toward the detector.

7. The gas concentration measurement device according to claim 5, wherein the surrounding frame includes a hole to receive the rotating shaft, and the rotating member includes an opposing wall that opposes the hole.

8. The gas concentration measurement device according to claim 5, wherein
    the surrounding frame includes a first surrounding frame and a second surrounding frame that are separate;
    the first surrounding frame defines a rotation space at a side near the detector;
    the second surrounding frame defines the rotation space at a side near the light source;
    the through hole is provided in the first surrounding frame; and
    the waveguide is provided on the second surrounding frame.

9. The gas concentration measurement device according to claim 8, wherein the rotating member includes an opposing wall that opposes a joining interface between the first surrounding frame and the second surrounding frame.

10. The gas concentration measurement device according to claim 5, wherein the detector includes a cavity through which the infrared light guided out of a through hole in the surrounding frame is guided toward the detector; and
    a projection of the through hole obtained when the through hole is projected toward the detector in an axial direction of the through hole does not overlap the cavity.

11. The gas concentration measurement device according to claim 1, further comprising a housing containing a sample cell in which the rotating member is disposed and the rotational driver.

12. The gas concentration measurement device according to claim 11, wherein the light source, the waveguide, the rotating member, and the detector are arranged in order from one end of the sample cell.

13. The gas concentration measurement device according to claim 1, wherein the rotating member includes a rotating holder.

14. The gas concentration measurement device according to claim 1, wherein the waveguide is made of a resin material having a reflectance of about 20% or less.

15. The gas concentration measurement device according to claim 1, wherein the first band pass filter transmits infrared light in a wavelength band different from that of the infrared light transmitted by the second band pass filter.

16. The gas concentration measurement device according to claim 1, wherein the rotational driver includes a stepper motor.

17. The gas concentration measurement device according to claim 1, wherein the detector is one of a thermopile and a bolometer.

18. The gas concentration measurement device according to claim 1, wherein an opening area of the entrance is greater than an opening area of the exit.

19. The gas concentration measurement device according to claim 1, wherein a portion of the inner peripheral surface of the wave-guiding portion defines a portion of a spherical surface between the entrance and the exit.

20. The gas concentration measurement device according to claim 1, wherein the inner peripheral surface of the wave-guiding portion includes a first curved portion and a second curved portion, and the wave-guiding portion includes a maximum circumference portion between the entrance and the exit.

* * * * *